United States Patent [19]
Duarte

[11] Patent Number: 4,530,360
[45] Date of Patent: Jul. 23, 1985

[54] METHOD FOR HEALING BONE FRACTURES WITH ULTRASOUND

[76] Inventor: Luiz R. Duarte, Rua Campos Sales 2099, Sao Paulo, Brazil, 13560

[21] Appl. No.: 441,237

[22] Filed: Nov. 12, 1982

[30] Foreign Application Priority Data

Nov. 19, 1981 [BR] Brazil .................................. 8107560

[51] Int. Cl.$^3$ .............................................. A61N 1/02
[52] U.S. Cl. .................................................. 128/419 F
[58] Field of Search ................. 128/24 A, 419 F, 783, 128/82.1

[56] References Cited

U.S. PATENT DOCUMENTS

| 2,799,787 | 7/1957 | Guttner et al. | 128/24 A |
| 3,499,437 | 3/1970 | Balamuth | 128/24 A |
| 4,175,565 | 11/1979 | Chiarenza et al. | 128/419 F |

OTHER PUBLICATIONS

Duarte, Ultrasonic Action on Callus Formation in Bones, 1975.
Duarte, Ultrasonic Stimulation of Fracture Healing, 1976.
Duarte, Ultrasound in the Treatment of Fractures, 1977.
Xavier et al., A Non-Invasive Form of Ultrasound Stimulation of Ununited Fractures, Sep. 1981.

*Primary Examiner*—Lee S. Cohen
*Attorney, Agent, or Firm*—Bradford E. Kile

[57] ABSTRACT

An apparatus and method for healing bone fractures, pseudoarthroses and the like with the use of ultrasound. An ultrasound transducer, in contact with the skin of the patient, transmits ultrasound pulses to the site of the bone defect. The nominal frequency of the ultrasound is 1.5 MHz, the width of each pulse varies between 10 and 2,000 microseconds, and the pulse repetition rate varies between 100 and 1,000 Hz. The power level of the ultrasound is maintained below 100 milliwatts per square centimeter. Treatments which last no more than about 20 minutes per day have been found to heal defects in a wide variety of cases in less than two months.

4 Claims, 2 Drawing Figures

METHOD FOR HEALING BONE FRACTURES WITH ULTRASOUND

BACKGROUND OF THE INVENTION

This invention relates to the healing of bone fractures, non-unions and pseudoarthroses, and more particularly to the healing thereof by the application of ultrasound.

In the past 25 years or so, many researchers have investigated techniques for promoting the healing of bone defects in both human beings and animals. For example, the application of direct current, in the order of 20 microamperes, at the site of a fracture is known to promote bone growth and thus healing. The cathode is usually applied at the site of the defect; the anode is placed somewhere in the adjacent tissue or on the skin of the patient. While such arrangements are totally or partially invasive, non-invasive techniques are also in use; an externally generated electromagnetic field is caused to pass through the fracture site, thus inducing a current which promotes healing.

The first approach suffers from the disadvantage of being at least partially invasive, while the second suffers from the disadvantage of requiring precise alignment of coils relative to the area to be treated as well as constant attention of medical personnel. Another disadvantage of the electromagnetic technique is that treatment is required for 12-16 hours per day. Furthermore, many months are usually required to achieve healing when using any of the prior art methods.

SUMMARY OF THE INVENTION

It is a general object of my invention to provide an improved apparatus and method for the treatment of non-unions, pseudoarthroses and other bone defects.

Briefly, in accordance with the principles of my invention, I utilize ultrasound energy to promote bone healing. The totally non-invasive technique of my invention involves placing an applicator on the skin of the patient, with an ultrasound transducer directing sound waves to the bone defect to be healed. The invention is based upon the fact that bone is piezoelectric in nature. Instead of inducing a current which promotes bone growth with an external electromagnetic field, or generating such a current directly, the mechanical energy of the ultrasound is converted to an electric current in the bone which then promotes healing.

Typical direct current bone growth stimulators, whether of the partially invasive or totally invasive type, apply current continuously, and at least three months of treatment are usually required. Electromagnetic treatments are usually 12-16 hours per day, and the total treatment time is usually longer. Treatment with ultrasound, in accordance with the principles of my invention, requires the application of ultrasound for approximately only 15-20 minutes per day, usually for less than 2 months. Not only is the bone defect healed much faster, but the ultrasound must be applied for only a very small part of each day. One of the advantages of the preferred apparatus is that it utilizes conventional technology. The transducer itself is of the same type used in conventional ultrasound diagnostic equipment. The transducer is contained at the end of an applicator which is applied to the skin of the patient, directly over the fracture site, with the use of a coupling gel (for example, of the same types of coupling gels used in ultrasound diagnostic applications). The electronic circuitry for energizing the transducer consists of conventional circuits, such as a radio frequency oscillator and a pulse generator to be described below.

After many years of investigation, I have discovered that for the most effective treatment certain operating characteristics must be maintained. The frequency of the ultrasound energy should be in the range 1.3-2 MHz. The energy should be applied in bursts; the width of each energy burst should be in the range 10-2,000 microseconds, and the burst or pulse repetition frequency should be in the range 100-1,000 Hz. Each daily treatment should have a duration in the range 1-55 minutes, although the preferred range is 10-20 minutes. It is also important that the ultrasound power be kept below a safety threshold so that the bone and adjacent tissue are not damaged. In this regard, it is a power density that is important, rather than an absolute total power level. (The total power, of course, is equal to the area of the transducer multiplied by the power per unit area; in the illustrative embodiment of the invention, the transducer is a circular disc whose outer diameter is 1 inch.)

The particular treatment in each case depends upon the type of defect to be healed. In the case of recent fractures, I employ ultrasound pulses which are 10 microseconds in duration and which occur at a repetition frequency of 500 Hz; a treatment of 10 minutes per day for a total of 30 days is often sufficient. In the case of a delayed healing, the daily and total times should be about the same, although the pulse width should be increased to 50 microseconds and the pulse repetition frequency should be increased to 1,000 Hz. A hypertrophic pseudoarthrosis requires a slightly longer daily treatment of 15 minutes and an even greater pulse width of 200 microseconds, although still using a 1,000-Hz pulse repetition frequency. In the case of an atrophic pseudoarthrosis, I have found that the most efficacious daily treatment consists of the application for 5 minutes of 200-microsecond pulses at a 1,000-Hz repetition frequency, followed by 15 minutes of the application of 2,000-microsecond pulses at a repetition frequency of 100 Hz; in such a case, the total treatment usually requires about 45 days.

An important benefit of the use of my invention is that pain experienced by the patient is usually relieved after only one week of daily stimulations. It should also be appreciated that my invention has application even if a cast is utilized; all that is necessary is to make a window in the cast directly above the fracture site. The application of ultrasound is effective even where a metallic implant for internal fixation has been used, provided that the metallic surface does not obstruct the path of the ultrasound. The invention is also applicable in cases where infections have developed.

Further objects, features and advantages of my invention will become apparent upon consideration of the following detailed description in conjunction with the drawing, in which:

DETAILED DESCRIPTION OF THE INVENTION

Figure 1:
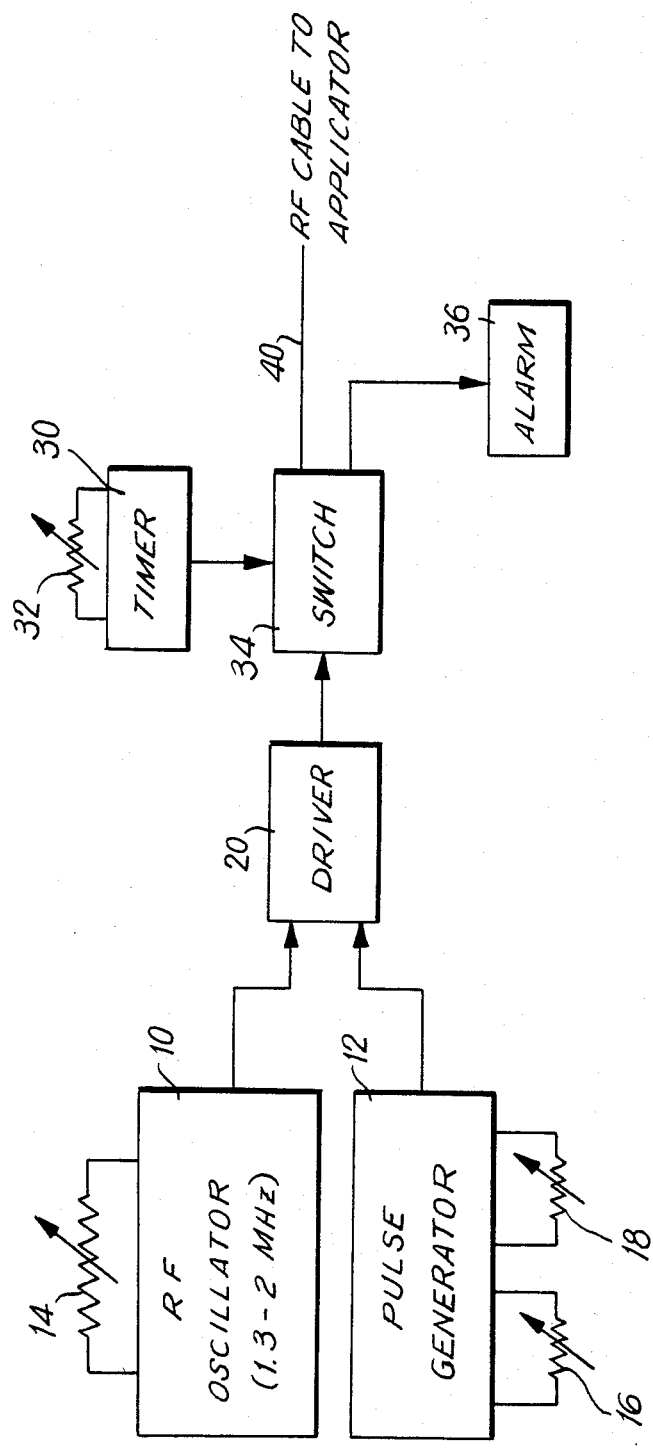
FIG. 1 is an electrical schematic of the illustrative embodiment of my invention.

The circuitry of FIG. 1 consists of standard electronic blocks, the details of none of which are important for an understanding of the present invention. The RF oscillator 10 generates a signal whose frequency is in the 1.3–2 MHz range. Potentiometer 14 symbolizes the manner in which the frequency can be varied within the two extreme limits. (Throughout the drawing, potentiometers are used to symbolize manual controls of variable parameters. In actual practice, thumbwheel switches or key inputs may be employed, as is known in the art.)

Pulse generator 12 has two variable inputs. Potentiometer 16 controls the repetition rate of the pulses generated by the device, and potentiometers 18 determines the width of each pulse. As described above, the pulse widths vary between 10 and 2,000 microseconds, and the pulse repetition frequency varies between 100 and 1,000 Hz.

The output of the oscillator and the output of the pulse generator are both coupled to driver 20. This device simply modulates the oscillator output with an envelope which is the waveform of the pulse generator signal. The driver output is thus a sine wave, having a frequency in the range 1.3–2 MHz, whenever the pulse generator generates a pulse. Driver 20 also amplifies the resulting signal so that the total power delivered to the applicator of FIG. 2 results in an ultrasound power level which has a maximum intensity of 100 milliwatts per square centimeter. Preferably, the power output should be near this level.

Timer 30 is set by potentiometer 32 to control the duration of the application of the RF signal to RF cable 40. Typical treatment times are 1–55 minutes, although treatments in the order of 10–20 minutes are the more usual. During the treatment time, the output of driver 20 is extended through switch 34 to cable 40. At the end of the treatment time, when the timer times out, switch 34 no longer extends the RF signal to cable 40, and instead energizes alarm 36. The alarm simply notifies the operator that the treatment is over.

Figure 2:
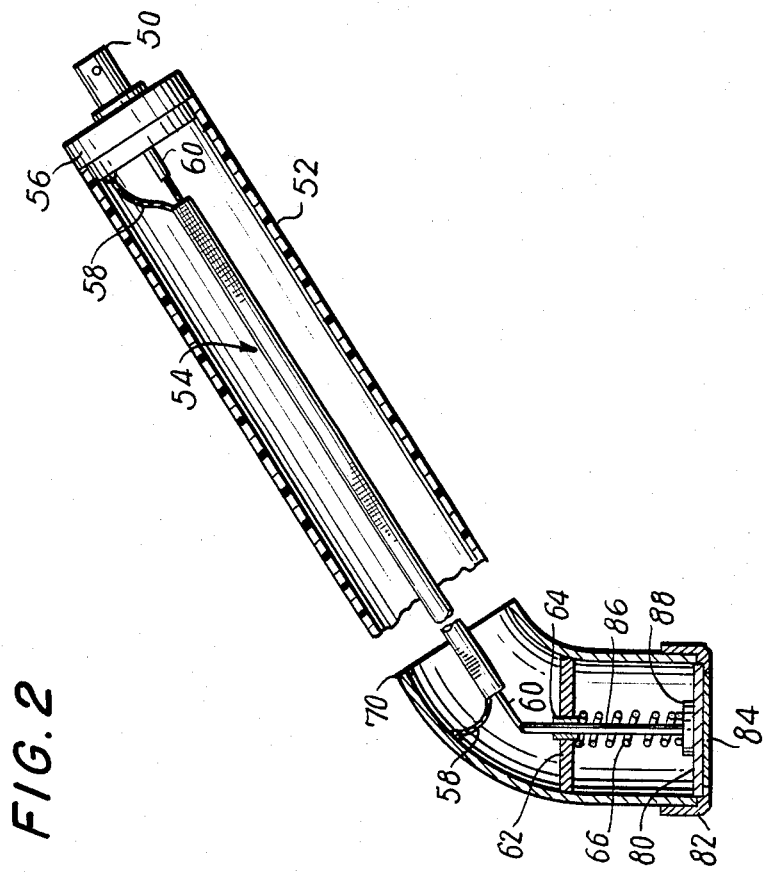
FIG. 2 depicts the ultrasound applicator which is energized by the circuitry of FIG. 1.

Cable 40 is extended to the applicator of FIG. 2, the cable being connected to standard RF plug 50. The plug is part of element 56 which fits in the end of plastic tube 52. The plastic tube serves as a grip for the operator.

The other end of the plastic tube is connected in any conventional manner to brass housing 70. Shielded cabel 54 has its center conductor 60 connected to the center contact of plug 50, with shielded wire 58 being connected to grounded conducting element 56. At the other end of the cable 54, the center conductor 60 is connected to pin 86, and the shielded wire is connected to the brass housing.

Pin 86 is supported by insulating bushing 64 which is contained in plate 62. At the end of the metallic pin, contact element 88 bears against transducer 80. The contact is biased against the transducer by spring 66.

The transducer element itself is made of conventional piezoelectric material such as PZT-4 (although the use of niobium instead of zirconium in the material composition is preferred). The upper face of transducer element 80 is silvered for making electrical contact with contact element 88. The outer rim of the bottom face is similarly silvered for making contact with stainless steel element 82, the latter being secured to housing 70 and serving to locate the transducer.

The thickness of the transducer material should be equal to one half of the wavelength of the frequency at which it vibrates. Although the RF signal can vary between 1.3 and 2 MHz, the nominal frequency is 1.5 MHz and the transducer element 80 should have a thickness equal to one half of the corresponding wavelength. Also, as is well known in the ultrasound diagnostic art, to maximize the coupling efficiency the front face of the transducer element should be secured to a layer of araldite 84 whose thickness should be equal to one quarter of the wavelength.

Prior to treatment, the region to which the applicator is to make contact should be shaved, and a coupling gel should be applied. The various potentiometers (or switches, etc.) are then set, and the applicator is held in place with maximum skin contact until the treatment is over.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

I claim:

1. A method for healing bone fractures, pseudoarthroses and like defects in a human patient comprising the step of applying a pulsed radio frequency ultrasound signal to the skin of a patient directed to the defect site, said pulsed radio frequency signal having a frequency in the range of 1.3–2 MHz, and consisting of pulses generated at a rate in the range 100–1,000 Hz, with each pulse having a duration in the range 10–2,000 microseconds.

2. A method in accordance with claim 1 wherein the power intensity of the ultrasound signal is no higher than 100 milliwatts per square centimeter.

3. A method in accordance with claim 2 wherein said pulsed radio frequency ultrasound signal is applied daily, for at least thirty days, for only a small part of each day.

4. A method in accordance with claim 1 wherein said pulsed radio frequency ultrasound signal is applied daily, for at least thirty days, for only a small part of each day.

* * * * *

UNITED STATES PATENT AND TRADEMARK OFFICE

CERTIFICATE EXTENDING PATENT TERM
UNDER 35 U.S.C. § 156

PATENT NO.      :  4,530,360

ISSUED          :  July 23, 1985

INVENTOR(S)     :  Luiz R. Duarte

PATENT OWNER :  Exogen, Inc.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

FIVE YEARS from the original expiration date of the patent, November 12, 2002, with all rights pertaining thereto as provided by 35 U.S.C. § 156(b).

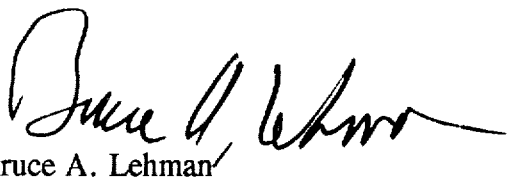

I have caused the seal of the Patent and Trademark Office to be affixed this 31st day of May 1996.

Bruce A. Lehman
Assistant Secretary of Commerce and
  Commissioner of Patents and Trademarks